United States Patent [19]

Miyazawa et al.

[11] Patent Number: 5,059,340
[45] Date of Patent: Oct. 22, 1991

[54] OPTICALLY ACTIVE 2-BIPHENYLPYRIMIDINE DERIVATIVE AND LIQUID CRYSTAL COMPOSITIONS CONTAINING SAME

[75] Inventors: Kazutoshi Miyazawa; Makoto Ushioda; Shinichi Saito; Hiromichi Inoue; Kouji Ohno, all of Kanagawa, Japan

[73] Assignee: Chisso Corporation, Osaka, Japan

[21] Appl. No.: 600,996

[22] Filed: Oct. 18, 1990

Related U.S. Application Data

[63] Continuation of Ser. No. 186,081, Apr. 25, 1988, abandoned.

[30] Foreign Application Priority Data

Apr. 27, 1987 [JP] Japan .................. 62-103977
Oct. 20, 1987 [JP] Japan .................. 62-264964

[51] Int. Cl.$^5$ ................................ C09K 19/34
[52] U.S. Cl. .................. 252/299.61; 252/299.01; 252/299.6; 544/298
[58] Field of Search .............. 252/299.61, 299.01, 252/299.6; 544/298; 350/350 S

[56] References Cited

U.S. PATENT DOCUMENTS

| | | | |
|---|---|---|---|
| 4,062,798 | 12/1977 | Boller et al. | 252/299.61 |
| 4,533,488 | 8/1985 | Fukui et al. | 252/299.61 |
| 4,744,918 | 5/1988 | Heppke et al. | 252/299.61 |
| 4,764,636 | 8/1988 | Sasaki et al. | 544/335 |
| 4,775,223 | 10/1988 | Yoshinaga et al. | 252/299.01 |
| 4,834,904 | 5/1989 | Krange et al. | 252/299.61 |
| 4,968,820 | 11/1990 | Scherowsky et al. | 544/298 X |
| 4,980,083 | 12/1990 | Shibata et al. | 252/299.61 |
| 4,985,172 | 1/1991 | Wingen et al. | 252/299.61 |
| 5,002,694 | 3/1991 | Wachtler et al. | 252/299.61 |

FOREIGN PATENT DOCUMENTS

| | | | |
|---|---|---|---|
| 206228 | 12/1986 | European Pat. Off. | 252/299.61 |
| 225195 | 6/1987 | European Pat. Off. | 252/299.61 |
| 248335 | 12/1987 | European Pat. Off. | 252/299.61 |
| 267585 | 5/1988 | European Pat. Off. | 252/299.01 |
| 3515373 | 11/1986 | Fed. Rep. of Germany | 252/299.61 |
| 240385 | 10/1986 | German Democratic Rep. | 252/299.61 |
| 240386 | 10/1986 | German Democratic Rep. | 252/299.61 |
| 63-22042 | 1/1988 | Japan | 252/299.61 |
| 63-183983 | 7/1988 | Japan | 252/299.61 |
| 8705012 | 8/1987 | World Int. Prop. O. | 252/299.01 |
| 8705018 | 8/1987 | World Int. Prop. O. | 252/299.61 |

OTHER PUBLICATIONS

Sato, S., et al., SID International Display Research Conference, pp. 107-110 (Oct. 4-6, 1988).

*Primary Examiner*—John S. Maples
*Assistant Examiner*—Richard Treanor
*Attorney, Agent, or Firm*—Wenderoth, Lind & Ponack

[57] ABSTRACT

An optically active compound having a large spontaneous polarization value and capable of affording a composition exhibiting a suitable ferroelectric liquid crystal temperature range and a liquid crystal composition containing the same are provided, which compound is expressed by the formula

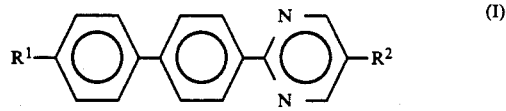

wherein either one of $R^1$ and $R^2$ represents an alkyl group or an alkoxy group each of 1 to 20 carbon atoms and another thereof represents an optically active group.

12 Claims, No Drawings

OPTICALLY ACTIVE 2-BIPHENYLPYRIMIDINE DERIVATIVE AND LIQUID CRYSTAL COMPOSITIONS CONTAINING SAME

This application is a continuation of now abandoned application Ser. No. 07/186,081 filed on Apr. 25, 1988.

BACKGROUND OF THE INVENTION

1. Field of the Invention

This invention relates to novel organic compounds and liquid crystal compositions containing the same, and more particularly it relates to organic compounds having an bptically active group and useful as a component of ferroelectric liquid crystal compositions and optically active liquid crystal compositions containing the same.

2. Description of the Related Art

At present, TN (Twisted Nematic) display mode has been most broadly employed, but it is inferior in the aspect of the response rate to emissive display elements such as electroluminescence, plasma display, etc. Thus, various attempts of improvement in this aspect have been made, but it does not appear that a possibility of the improvement to a large extent remains so much.

Thus, various liquid crystal display devices based on a different principle have been attempted, and as one of them, a display method utilizing ferroelectric liquid crystals is proposed (N. A. Clark et al; Applied Phys., lett., 36, 899 (1980)). This mode utilizes ferroelectric chiral smectic C phase (hereinafter abbreviated to SC* phase) or other smectic phases such as SH* phase, SF* phase, SG* phase, etc. and has the following three superior specific features as compared with TN display mode:

a first specific feature consists in that it has a very high response rate amounting to 100 times that of TN display elements; a second specific feature consists in that it has a memory effect so that multiplex drive is easy in combination with the above high rate response properties; and a third specific feature consists in that it is possible to obtain gray scale more easily than TN display mode only by adjusting the inversion time of polarity; hence the mode has been considered to be suitable for graphic display.

However, in spite of such superior specific features, as to currently known ferroelectric liquid crystal compounds and compositions, those satisfying both of the following two conditions have not yet been obtained:

Namely, they have a large spontaneous polarization value required for obtaining the high rate response properties as the first specific feature of ferroelectric liquid crystal compounds as well as a liquid crystal temperature range suitable for practical use. For example, when a compound,

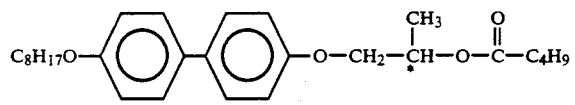

as one of compounds disclosed in Japanese patent application No. Sho 61-133269/1986, the invention of which has been made by the present inventors, was added in 20% by weight to a composition exhibiting achiral smectic C phase, the resulting composition exhibited a response rate of 48 μsec at 25° C.; thus it may be said that the compound has approached a stage of practical use. However, reduction in the upper limit temperature of the ferroelectric liquid crystal phase amounted to as high as 20° C. as compared with that prior to the addition of the compound; hence the problem of its practical use has still been left behind. This is because a compound having a large spontaneous polarization value and a preferred mesomorphic range has not yet been found.

SUMMARY OF THE INVENTION

The object of the present invention is to provide a liquid crystal compound capable of affording a liquid crystal composition having specific features suitable to the above-mentioned display mode, particularly a large spontaneous polarization value, and also exhibiting a suitable ferroelectric mesomorphic range.

The present inventors have made extensive research in order to develop an optically active liquid crystal compound suitable for being utilized for the display mode, and have achieved the present invention.

The present invention resides in an optically active compound expressed by the formula

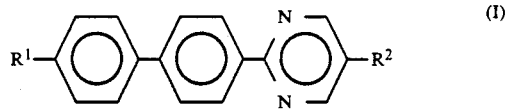

wherein either one of $R^1$ and $R^2$ represents an alkyl group or an alkoxy group each of 1 to 20 carbon atoms and the other thereof represents an optically active group, and a liquid crystal composition containing at least one member of the same.

The optically active compounds of the formula (I) can be roughly classified into the following two compound groups expressed by the formulas (I-A) and (I-B), depending on the site of the optically active group:

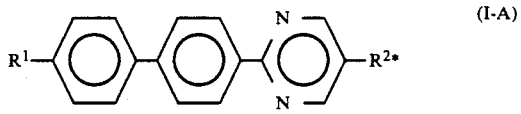

wherein $R^{2*}$ represents an optically active group, and

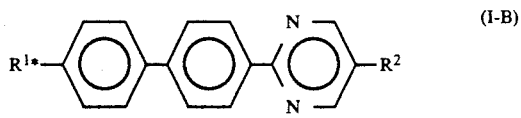

wherein $R^{1*}$ represents an optically active group.

DETAILED DESCRIPTION OF PREFERRED EMBODIMENTS

Representatives of the compounds of the formula (I) of the present invention and their phase transition points are shown in Table 1.

TABLE 1

| Compound No. | In formula (I) R¹ | In formula (I) R² | Absolute configuration | Phase transition points (°C.) C | $S_X$ | $S_C^*$ | $S_A$ | Ch | I | Note |
|---|---|---|---|---|---|---|---|---|---|---|
| 1 | $C_5H_{11}$— | —CH$_2$CHCH$_2$CH$_3$ <br>            \|<br>           CH$_3$ | S | • 84.5 | SG • 85.9 | — | — | • 133.2 | • | Example 4 |
| 2 | $C_5H_{11}$— | —(CH$_2$)$_3$CHCH$_2$CH$_3$<br>               \|<br>               CH$_3$ | S | • 80.0 | $S_E$ • 83.0 | — | • 122.6 | — | • | |
| 3 | $C_3H_7$— | —O(CH$_2$)$_3$CHCH$_2$CH$_3$<br>                \|<br>                CH$_3$ | S | • 129.0 | — | — | — | • 166.1 | • | |
| 4 | $C_3H_7$— | —O(CH$_2$)$_4$CHCH$_2$CH$_3$<br>                \|<br>                CH$_3$ | S | • 95.6 | — | • 118.1 | — | • 160.4 | • | |
| 5 | $C_3H_7$— | —O(CH$_2$)$_5$CHCH$_2$CH$_3$<br>                \|<br>                CH$_3$ | S | • 85.0 | — | • 139.8 | — | • 167.3 | • | Example 2 |
| 6 | $C_3H_7$— | —O(CH$_2$)$_7$CHCH$_2$CH$_3$<br>                \|<br>                CH$_3$ | S | • 123.0 | — | • 151.2 | — | • 165.0 | • | |
| 7 | $C_3H_7$— | —O—CH(CH$_2$)$_5$CH$_3$<br>          \|<br>          CH$_3$ | S | • 48.0 | — | — | — | • 73.3 | • | |
| 8 | $C_3H_7$— | —OCH—(CH$_2$)$_5$CH$_3$<br>      \|<br>      CH$_2$CH$_3$ | R | • 29.2 | — | — | — | — | • | |
| 9 | $C_6H_{13}$— | —O(CH$_2$)$_5$CHCH$_2$CH$_3$<br>                \|<br>                CH$_3$ | S | • 66.0 | — | • 149.5 | — | • 161.3 | • | |
| 10 | $C_6H_{13}$— | —OCH—(CH$_2$)$_5$CH$_3$<br>     \|<br>     CH$_3$ | S | • 31.8 | — | — | — | • 66.5 | • | |
| 11 | $C_6H_{13}O$— | —O—(CH$_2$)$_5$CHCH$_2$CH$_3$<br>                 \|<br>                 CH$_3$ | S | • 108.1 | — | • 169.3 | — | • 182.1 | • | |

TABLE 1-continued

| Compound No. | In formula (I) R¹ | R² | Absolute configuration | Phase transition points (°C.) C | $S_X$ | $S_C*$ | $S_A$ | Ch | I | Note |
|---|---|---|---|---|---|---|---|---|---|---|
| 12 | $C_6H_{13}O-$ | $-O(CH_2)_7\overset{*}{C}HCH_2CH_3$ with $CH_3$ | S | • 92.4 | — | • 175.1 | — | • 181.3 | • | |
| 13 | $C_5H_{11}-$ | $-O-CH_2\overset{*}{C}HO-(CH_2)_3CH_3$ with $CH_3$ | R | • 54.9 | — | • 67.6 | — | • 92.5 | • | |
| 14 | $C_5H_{11}-$ | $-O-CH_2\overset{*}{C}HO-(CH_2)_3CH_3$ with $CH_3$ | R | • 41.0 | — | • 59.8 | — | • 88.1 | • | |
| 15 | $C_5H_{11}-$ | $-O\overset{*}{C}H_2\overset{*}{C}H-(CH_2)_5CH_3$ with F | S | • 106.3 | — | • 156.2 | — | • 180.9 | • | |
| 16 | $C_7H_{15}-$ | $-O\overset{*}{C}H\,CO-CH_2CH_3$ with $CH_3O$ | R | • 86.6 | — | — | — | — | • | |
| 17 | $C_3H_7-$ | $-OC-(CH_2)_4\overset{*}{C}HCH_2CH_3$ with $O=$ and $CH_3$ | S | • 90.0 | (• 88.5) | — | — | • 170.4 | • | Example 3 |
| 18 | $C_6H_{13}-$ | $-OC-(CH_2)_4\overset{*}{C}HCH_2CH_3$ with $O=$ and $CH_3$ | S | • 72.6 | • 80.5 | • 150.5 | — | • 161.7 | • | |
| 19 | $C_6H_{13}O-$ | $-OC-(CH_2)_2\overset{*}{C}HCH_2CH_3$ with $O=$ and $CH_3$ | S | • 114.0 | • 116.0 | • 159.4 | — | • 185.0 | • | |
| 20 | $C_6H_{13}O-$ | $-OC-(CH_2)_4\overset{*}{C}HCH_2CH_3$ with $O=$ and $CH_3$ | S | • 95.0 | (• 89.0) | • 168.0 | — | • 186.1 | • | |
| 21 | $C_3H_7-$ | $-OC-\overset{*}{C}HO-(CH_2)_3CH_3$ with $O=$ and $CH_3$ | S | • 107.9 | — | — | — | — | • | |
| 22 | $C_6H_{13}-$ | $-OC-\overset{*}{C}HO-(CH_2)_3CH_3$ with $O=$ and $CH_3$ | S | • 113.3 | — | — | — | — | • | |

TABLE 1-continued

| Compound No. | In formula (I) R¹ | In formula (I) R² | Absolute configuration | Phase transition points (°C.) C | Sₓ | Sc* | S_A | Ch | I | Note |
|---|---|---|---|---|---|---|---|---|---|---|
| 23 | C₆H₁₃— | —OC—CHO—(CH₂)₄CH₃ with O=, CH₃, * | S | • 110.0 | — | — | — | — | • | |
| 24 | C₆H₁₃O— | —OC—CHO—(CH₂)₄CH₃ with O=, CH₃, * | S | • 131.0 | — | • 135.0 | — | — | • | |
| 25 | C₃H₇— | —OCH₂CHOC—(CH₂)₃CH₃ with CH₃, O=, * | S | • 98.5 | — | — | — | (• 70.0) | • | Example 1 |
| 26 | C₃H₇— | —OCH₂CHOC—(CH₂)₄CH₃ with CH₃, O=, * | S | • 94.0 | — | — | — | — | • | |
| 27 | C₃H₇— | —OCH₂CHOC—(CH₂)₅CH₃ with CH₃, O=, * | S | • 77.4 | — | — | — | — | • | |
| 28 | C₃H₇— | —OCH₂CHOC—(CH₂)₉CH₃ with CH₃, O=, * | S | • 82.9 | — | — | — | — | • | |
| 29 | C₆H₁₃— | —OCH₂CHO—C—(CH₂)₃CH₃ with CH₃, O=, * | S | • 68.4 | — | • 70.5 | — | — | • | |
| 30 | C₇H₁₅— | —OCH₂CHOC—(CH₂)₃CH₃ with CH₃, O=, * | S | • 76.5 | — | (• 73.3) | — | • 79.0 | • | |
| 31 | C₆H₁₃O— | —OCH₂CHOC—(CH₂)₃CH₃ with CH₃, O=, * | S | • 86.4 | (• 66.2) | • 114.2 | — | — | • | |
| 32 | C₆H₁₃O— | —OCH₂CHOC—(CH₂)₄CH₃ with CH₃, O=, * | S | • 81.2 | (• 62.8) | • 109.4 | — | — | • | |
| 33 | C₃H₇— | —OCH₂CHOC—(CH₂)₂CHCH₃ with CH₃, O=, CH₃, * | S | • 101.5 | — | — | — | — | • | |

TABLE 1-continued

| Compound No. | In formula (I) R¹ | In formula (I) R² | Absolute configuration | Phase transition points (°C.) C | $S_X$ | $S_C^*$ | $S_A$ | Ch | I | Note |
|---|---|---|---|---|---|---|---|---|---|---|
| 34 | $C_3H_7-$ | $-OCH_2\overset{*}{C}HOC-(CH_2)_2CHCH_2CH_3$ with $CH_3$, $O=$, $CH_3$ | S,S | • 91.4 | — | — | — | — | • | |
| 35 | $C_3H_7-$ | $-OCH_2\overset{*}{C}HOC-(CH_2)_4CHCH_2CH_3$ with $CH_3$, $O=$, $CH_3$ | S,S | • 76.5 | — | — | — | — | • | |
| 36 | $C_5H_{11}-$ | $-OCH_2\overset{*}{C}HOCCH_2CHCH_2CH_3$ with $CH_3$, $O=$, $CH_3$ | S,S | • 88.9 | — | — | — | — | • | |
| 37 | $C_5H_{11}-$ | $-OCH_2\overset{*}{C}H-OCCH_2CHCH_2CH_3$ with $CH_3$, $O=$, $CH_3$ | R,S | • 86.5 | — | — | — | — | • | |
| 38 | $C_3H_7-$ | $-OCH_2\overset{*}{C}HOC-CH-O(CH_2)_3CH_3$ with $CH_3$, $O=$, $CH_3$ | S,S | • 85.3 | — | — | — | (• 74.4) | • | |
| 39 | $C_3H_7-$ | $-OCH_2\overset{*}{C}HOC-CHO(CH_2)_5CH_3$ with $CH_3$, $O=$, $CH_3$ | S,S | • 72.8 | — | — | — | (• 67.4) | • | |
| 40 | $C_5H_{11}-$ | $-OCH_2\overset{*}{C}HOC-CHO(CH_2)_3CH_3$ with $CH_3$, $O=$, $CH_3$ | S,R | • 78.5 | — | — | — | — | • | |
| 41 | $C_5H_{11}-$ | $-OCH_2\overset{*}{C}HOC-CHO(CH_2)_3CH_3$ with $CH_3$, $O=$, $CH_3$ | S,S | • 71.0 | — | — | — | (• 80.0) | • | |
| 42 | $C_6H_{13}-$ | $-OCH_2\overset{*}{C}H-OC-CHO(CH_2)_3CH_3$ with $CH_3$, $O=$, $CH_3$ | S,S | • 80.5 | — | — | — | (• 73.5) | • | |
| 43 | $C_6H_{13}-$ | $-OCH_2\overset{*}{C}HOC-CHO-(CH_2)_4CH_3$ with $CH_3$, $O=$, $CH_3$ | S,S | • 60.3 | — | — | — | (• 71.0) | • | |
| 44 | $C_6H_{13}-$ | $-OCH_2\overset{*}{C}HOC-CHO-(CH_2)_5CH_3$ with $CH_3$, $O=$, $CH_3$ | S,S | • 69.0 | — | — | — | (• 68.0) | • | |

TABLE 1-continued

| Compound No. | In formula (I) R¹ | In formula (I) R² | Absolute configuration | Phase transition points (°C.) C | Sx | Sc* | SA | Ch | I | Note |
|---|---|---|---|---|---|---|---|---|---|---|
| 45 | C₇H₁₅— | —OCH₂CHOC—CHO—(CH₂)₃CH₃ (with CH₃ O CH₃) | S,S | • 74.4 | — | (• 64.7) | — | • 81.6 | • | |
| 46 | C₆H₁₃O— | —OCH₂CHOC—CHO—(CH₂)₃CH₃ (with CH₃ O CH₃) | S,S | • 88.3 | — | • 103.8 | — | • 112.8 | • | |
| 47 | C₆H₁₃O— | —OCH₂CHOC—CHO—(CH₂)₅CH₃ (with CH₃ O CH₃) | S,S | • 66.8 | — | • 95.0 | — | • 107.0 | • | |
| 48 | CH₃(CH₂)₅CHO— (with CH₃) | —C₈H₁₇ | S | • 73.2 | — | — | • 100.7 | — | • | |
| 49 | CH₃CH₂CH—(CH₂)₇—O— (with CH₃) | —C₇H₁₅ | S | • 85.8 | — | • 148.2 | — | • 159.3 | • | |
| 50 | CH₃(CH₂)₃CO—CHCH₂O— (with O CH₃) | —C₈H₁₇ | S | • 104.0 | — | • 135.0 | • 111.3 | — | • | |
| 51 | CH₃(CH₂)₃OCH CO—CHCH₂O— (with CH₃O CH₃) | —C₆H₁₃ | S,S | • 71.0 | — | — | • 87.8 | • 90.1 | • | |
| 52 | CH₃(CH₂)₃OCH CO—CHCH₂O— (with CH₃O CH₃) | —C₈H₁₇ | S,S | • 68.4 | — | — | • 103.8 | — | • | |
| 53 | CH₃(CH₂)₅CHCH₂O— (with F) | —C₇H₁₅ | S | • 91.8 | • 116.0 | • 150.7 | — | • 169.5 | • | |

The compounds of the present invention includes both compounds exhibiting liquid crystal phase and those exhibiting no liquid crystal phase, but at any rate the first specific feature of the compound consists in that is has a large spontaneous polarization value. For example, compound No. 47 listed above has a large spontaneous polarization value as shown in the following Table; hence the compound can be said to be a very useful compound.

TABLE 2

| Temperature (°C.) | 90.5 | 85.5 | 80.5 | 75.5 | 70.5 |
|---|---|---|---|---|---|
| Spontaneous polarization value (nC/cm$^2$) | 285 | 327 | 346 | 374 | 388 |

When any of the compounds of the present invention is used as a component of ferroelectric liquid crystal compositions, it has a function of notably increasing the spontaneous polarization values thereof so that it is possible to shorten the response rates. As will be described later in the Examples, when the compound is added in several % to several tens % by weight to liquid crystal compositions exhibiting no spontaneous polarization value and also exhibiting achiral smectic C phase, the resulting compositions have a large spontaneous polarization values induced. For example, as described in Example 5, it is possible to obtain a composition having a response rate as extremely short as 125 μsec at 25° C. For example, as compared with the fact that a compound

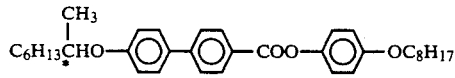

disclosed in Japanese patent application laid-open No. Sho 61-43/1986 (Japanese patent application No. Sho 59-119590/1984), the invention of which has been made by the present inventors, singly has a spontaneous polarization value as considerably large as 89 nC/cm$^2$ and nevertheless when the compound is added in 30% by weight to a liquid crystal composition exhibiting achiral smectic C phase, the resulting composition exhibits a response rate of only 2 μsec, it is seen that the compound of the present invention has a far superior specific feature.

Further, some of the compounds of the present invention have a suitable ferroelectric liquid crystal range; hence it is possible to provide a ferroelectric liquid crystal range suitable as a component of compositions. Further, even in the case of compounds having no ferroelectric liquid crystal range among the compounds of the present invention, when the compounds are added to other compositions exhibiting a chiral smectic C phase, they do not reduce the upper limit temperature of the resulting chiral smectic C phase, but rather have an effectiveness of making extinct the smectic A phase as a non-ferroelectric liquid crystal phase existent on the higher temperature side relative to chiral smectic C phase; hence it can be said that the compounds are very useful.

Further, since the compound of the present invention has an optically active carbon atom, it has a capability of inducing a twisted structure when it is added to a nematic liquid crystal. Nematic liquid crystals having a twisted structure, i.e., chiral nematic liquid crystals do not form the so-called reverse domain of TN mode display elements; hence the compound of the present invention is usable as an agent for preventing the reverse domain from forming.

Further, as to the pitch of chiral nematic liquid crystals obtained by adding the compound of the present invention, for example, as shown in Example 8, when compound No. 26 of the present invention was added in 1% by weight to ZLI-1132 manufactured by Merck Company and the pitch of the resulting composition was measured, the pitch was as short as 11.7 μm at 30° C., that is, by adding a lower quantity, a necessary pitch is easily obtained; hence the compound can be said to be very useful as an agent for adjusting the pitch of chiral nematic liquid crystal compositions.

Further, its temperature-dependency was very good, that is, the temperature-dependency δp expressed by the formula $$\delta p = \frac{2(p(t_1) - p(t_2))}{p(t_1) + p(t_2)} \times \frac{100}{t_1 - t_2}$$

wherein p(t): pitch at t° C., t: temperature) was as very small as 0.123 ($t_1=20°$ C. and $t_2=70°$ C.). This is a surprising specific feature, for example as compared with the case where an agent for adjusting the pitch of currently well known chiral nematic liquid crystal compositions, (S)-4-(2'-methyl-butyl)-4'-cyanobiphenyl, has a δp of 0.584 under the same conditions. These superior specific features of the compound of the present invention is considered to originate in

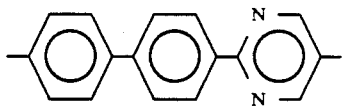

as its core, and as to the optically active group as a substituent introduced into its 5-or 4'-position, the following groups may be exemplified:

optically active alkyl group, optically active alkoxy group, optically active alkanoyloxy group, optically active alkoxycarbonyloxy group, optically active halogen-substituted alkyl group, optically active halogen-substituted alkoxy group, optically active halogen-substituted alkanoyloxy group, optically active halogen-substituted alkoxycarbonyloxy group, optically active cyano-substituted alkyl group, optically active cyano-substituted alkoxy group, optically active cyano-substituted alkanoyloxy group, optically active cyano-substituted alkoxycarbonyloxy group, optically active alkoxyalkyl group, optically active alkanoyloxyalkyl group, optically active alkoxyalkoxy group, optically active alkanoyloxyalkoxy group, optically active alkoxyalkanoyloxy group, optically active halogen-substituted alkoxyalkyl group, optically active cyano-substituted alkoxyalkyl group, optically active halogen-substituted alkanoyloxyalkyl group, optically active cyano-substituted alkanoyloxyalkyl group, optically active halogen-substituted alkoxyalkoxy group, optically active cyano-substituted alkoxyalkoxy group, optically active halogen substituted alkanoyloxyalkoxy group, optically active cyanosubstituted alkanoyloxyalkoxy group, optically active halogen-substituted alkoxyalkanoyloxy group, optically active cyano-substituted alkoxyalkanoyloxy group, optically active alkoxycarbonyl group, optically active halogen-substituted alkoxycarbonyl group, optically active cyano-substituted alkoxycarbonyl group, optically active alkoxyalkoxycarbonyl group, optically active halogen-substituted alkoxyalkoxycarbonyl group, optically active cyano-substituted alkoxyalkoxycarbonyl group, etc.

When the fact that the superior specific features of the compound of the present invention originate in the central core of the compound as described above is taken into consideration, it is readily understandable that any of the compounds having an optically active group as described above introduced thereinto have the same superior specific features, as described in Examples.

Here, the relation between the compound of the present application and the compound disclosed in Japanese patent application laid-open No. Sho 61-44845/1986 as a prior application thereto will be referred to. The prior application discloses a general formula including an astronomical number of corpounds, and the compound of the present invention may also be formally included in the formula, but the publication of the application does not disclose the same compound as that of the present invention not only concretely, but also as a general formula having developed the general formula (I). Further, the aimed effectiveness of the compound of the prior application consists in that cholesteric phase is induced by adding the compound to a nematic liquid crystal to thereby improve the temperature-dependency of the pitch thereof; hence the effectiveness has nothing to do with ferroelectric liquid crystals aimed in the present invention. Thus, it cannot be said that the compound of the present invention is disclosed in the prior application.

The compounds of the formula (I) of the present invention may be prepared through the following routes:

A)

A-a) In the case where $R^{2*}$ in the formula (I-A) represents an optically active alkyl group, an optically active halogen-substituted alkyl group or an optically active cyano-substituted alkyl group:

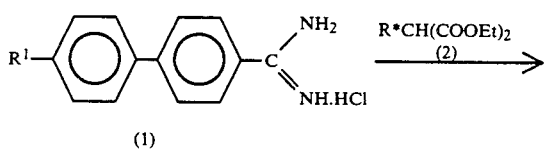

(1)

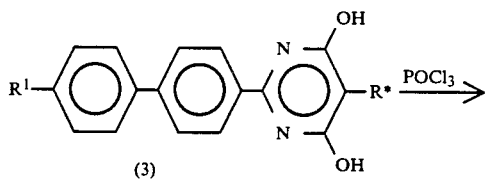

(3)

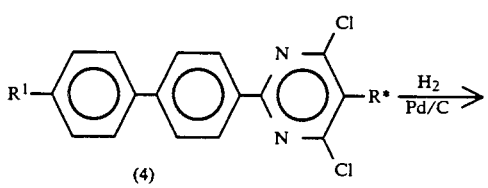

(4)

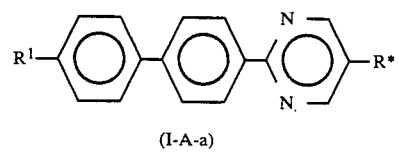

(I-A-a)

wherein R* represents the above-mentioned optically active alkyl group, optically active halogen-substituted alkyl group or optically active cyano-substituted alkyl group.

Namely, compound (2) is reacted with compound (1) to obtain compound (3), followed by reacting a chlorinating agent such as an oxychloride with the compound (3) to obtain a compound (4) which is then reduced in the presence of a catalyst to obtain the objective compound of the formula (I-A-a).

Representatives of the compounds of the formula (I-A-a) prepared according to the above process are as follows:

(S)-5-(4'-methylhexyl)-2-(4'-octyl-biphenyl-4-yl)pyrimidine, (R)-5-(5'-methylheptyl)-2-(4'-pentyl-biphenyl-4-yl)pyrimidine, (S)-5-(8'-methyldecyl)-2-(4'-nonyl-biphenyl-4-yl)pyrimidine, (R)-5-(6'-methyloctyl)-2-(4'-octyloxy-biphenyl-4-yl)pyrimidine, (S)-5-(7'-methynonyl)-2-(4'-undecyloxy-biphenyl-4-yl)pyrimidine, (S)-5-(2'-methybutyl)-2-(4'-pentyl-biphenyl-4-yl)pyrimidine, (Compound No. 1)

(S)-5-(4'-metylhexyl)-2-(4'-pentyl-biphenyl-4-yl)pyrimidine, (Compound No. 2)

A-b) In the case where $R^{2*}$ in the formula (I-a) represents an optically active alkoxy group, optically active halogen-substituted alkoxy group, or optically active cyano-substituted alkoxy group:

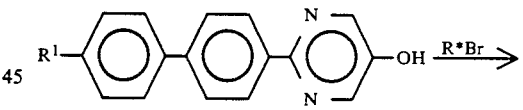

(5)

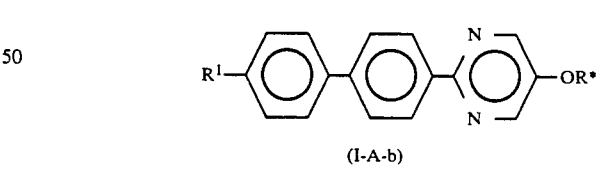

(I-A-b)

wherein R* in the above formulas represents the above-mentioned optically alkyl group, optically active halogen-substituted alkyl group or optically active cyano-substituted alkyl group.

Namely, an alkyl halide such as an alkyl bromide, an alkyl tosylate or the like is reacted with compound (5) under a basic condition to introduce an alkyl group and thereby obtain a compound of the formula (I-A-b).

Representatives of the compound of the formula (I-A-b) prepared according to the above process are as follows:

(S)-5-(4'-methylhexyloxy)-2-(4'-propyl-biphenyl-4-yl)pyrimidine, (Compound No. 3)

(S)-5-(5'-methylheptyloxy)-2-(4'-propyl-biphenyl-4-yl)pyrimidine, (Compound No. 4)

(S)-5-(6'-methyloctyloxy)-2-(4'-propyl-biphenyl-4-yl)pyrimidine, (Compound No. 5)

(S)-5-(8'-methyldecyloxy)-2-(4'-propyl-biphenyl-4-yl)pyrimidine, (Compound No. 6)

(S)-5-(1'-methylheptyloxy)-2-(4'-propyl-biphenyl-4-yl)pyrimidine, (Compound No. 7)

(R)-5-(9'-methylundecyloxy)2-(4'-pentyl-biphenyl-4-yl)pyrimidine, (S)-5-(8'-methyldecyloxy)-2 (4'-nonyl-biphenyl-4-yl)pyrimidine, (S)-5-(6'-methyloctyloxy)-2-(4'-octyl-biphenyl-4-yl)pyrimidine, (S)-5-(6'-methyloctyloxy)-2-(4'-hexyloxy-biphenyl-4-yl)pyrimidine, (Compound No. 11)

(S)-5-(8'-methyldecyloxy)-2-(4'-hexyloxy-biphenyl-4-yl)pyrimidine, (Compound No. 12)

(R)-5-(7'-methylnonyloxy)-2-(4'-octyloxy-biphenyl-4-yl)pyrimidine, (S)-5-(5'-methylheptyloxy)-2-(4'-undecyloxy-biphenyl-4yl)pyrimidine, (S)-5-(6'-methyloctyloxy)-2-(4'-hexyl-biphenyl-4-yl)pyrimidine, (Compound No. 9)

(S)-5-(1'-methylheptyloxy)-2-(4'-hexyl-biphenyl-4-yl)pyrimidine, (Compound No. 10)

(S)-5-(1'-ethoxycarbonylethoxy)-2-(4'-heptyl-biphenyl-4-yl)pyrimidine, (S)-5-(2'-fluorooctyloxy)-2(4'-pentyl-biphenyl-4-yl)pyrimidine, (Compound No. 15)

(S)-5-(2'-fluorooctyloxy)-2-(4'-hexyloxy-biphenyl-4-yl)pryimidine.

A-c) In the case where $R^{2*}$ in the formula (I-A) represents an optically active alkanoyloxy group, an optically active halogen-substituted alkanoyloxy group or an optically active cyano-substituted alkanoyloxy group:

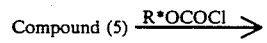

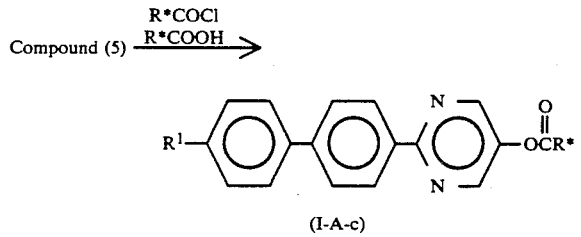

(I-A-c)

wherein R* in the above formula represents the above-mentioned optically alk.vl group, optically active halogen-substituted alkyl group.or optically active cyano-substituted alkyl group.

Namely, an alkanoic acid or an alkanoic acid halide such as an alkanoic acid chloride is reacted with compound (5) to obtain a compound of the formula (I-A-c).

Representatives of the compound of the formula (I-A-c) prepared according to the above process are as follows:

(S)-5-(6'-methyloctanoyloxy)-2-(4'-propyl-biphenyl-4-yl)pyrimidine, (Compound No. 17)

(S)-5-(8'-methyldecanolyoxy)2-(4'-nonyl-biphenyl-4-yl)pyrimidine, (R)-5-(6'-methyloctanoyloxy)-2-(4'-octyl-biphenyl-4-yl)pyrimidine, (S)-5-(4'-methylhexanoyloxy)-2-(4'-hexyloxy-biphenyl-4-yl)pyrimidine, (Compound No. 19)

(S)-5-(6'-methyloctanoyloxy)-2-(4'-hexyl-biphenyl-4-yl)pyrimidine, (Compound No. 18)

(2'S,3'S)-5-(3'-methylvaleryloxy)-2-(4'-propyl-biphenyl-4-yl)-pyrimidine, (2'S,3'S)-5-(2'-chloro-3'-methylvaleryloxy) -2-(4'-heptyl-biphenyl-4-yl)-pyrimidine, (2'S,3'S)-5-(2'-chloro-3'-methylvaleryloxy) -2-(4'-octyl-biphenyl-4-yl)-pyrimidine, (S)-5-(6'-methyloctanoyloxy)-2-(4'-hexyloxy-biphenyl-4-yl) pyrimidine, (Compound No. 20)

A-d) In the case where $R^{2*}$ in the formula (I-A) represents an optically active alkoxycarbonyloxy group, an optically active halogen-substituted alkoxycarbonyloxy group or an optically active cyano-substituted alkoxycarbonyloxy group:

Compound (5) $\xrightarrow{R*OCOCl}$

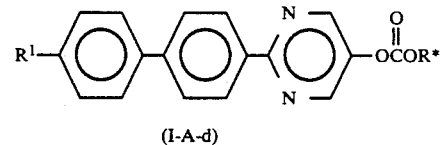

(I-A-d)

wherein R* in the above formula represents the above-mentioned optically alkyl group, optically active halogen-substituted alkyl group or optically active cyano-substituted alkyl group.

Namely, an alkyl chloroformate is reacted with compound (5) to obtain a compound of the formula (I-A-d).

Representatives of the compounds of the formula (I-A-d) prepared according to the above process are as follows:

(S)-5-(4'-methylhexyloxycarbonyloxy)-2-(4'-octyl-biphenyl-4-yl)pyrimidine, (S)-5-(8'-methyldecyloxycaronyloxy)-2-(4'-octyloxy-biphenyl-4-yl)pyrimidine, (S)-5-(1'-methylheptyloxycarbonyloxy)-2-(4'-nonyl-biphenyl-4-yl)pyrimidine, (S)-5-(2'-methylbutoxycarbonyloxy)-2-(4'-undecyloxy-biphenyl-4yl)pyrimidine, A-e) In the case where $R^{2*}$ in the formula (I-A) represents an optically active alkoxyalkyl group, an optically active halogen-substituted alkoxyalkyl group or an optically active cyano-substituted alkoxyalkyl group:

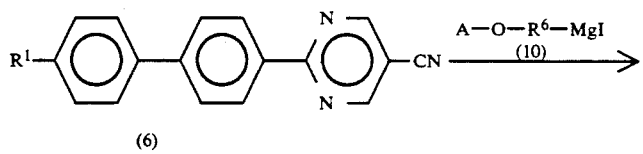

(6)

-continued

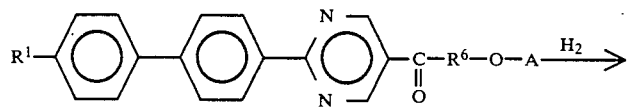

(7)

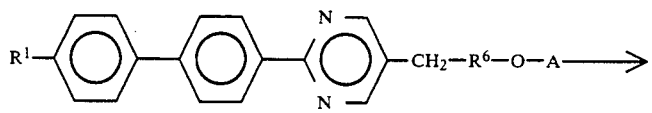

(8)

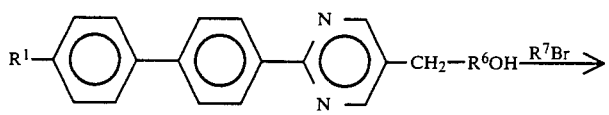

(9)

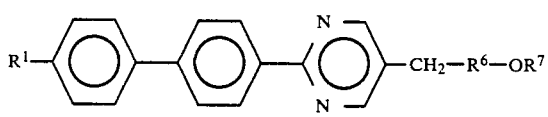

(I-A-e)

wherein R⁷ in the above formulas represents an alkyl group, a halogen-substituted alkyl group or a cyano-substituted alkyl group; R⁶ represents a divalent hydrocarbon radical, a divalent halogen-substituted hydrocarbon radical or a divalent cyano-substituted hydrocarbon radical; A represents a protecting group such as benzyl group, tetrahydropyranyl group; and at least one of R⁶ and R⁷ has an asymmetric carbon atom.

Namely, a Grignard reagent (10) is reacted with compound (6) to obtain a compound (7), which is then reduced into a compound (8), which is then subjected to removal of the protecting group to obtain a compound (9), followed by reacting therewith an alkyl halide such as an alkyl bromide, an alkyl tosylate or the like to obtain the objective compound of the formula (I-A-e).

Representatives of the compound of the formula (I-A-e) prepared according to the above process are as follows:

(R)-5-(2'-(8'-methydecyloxy)ethy)-2-(4'-nonyl-biphenyl-4-yl)pyrimidine, (2''S, 6''S)-5-(2'-(6''-metyloctyloxy) propyl)-2-(4'-octyl-biphenyl-4-yl)-pyrimidine, (3'S, 7''S)-5-(3'-(7''-metylnonyloxy)butyl) -2-(4'-pentyloxy-biphenyl-4-yl)-pyrimidine, (4'S, 4''S)-5-(4'-(4''-metylhexyloxy)pentyl) -2-(4'-pentyloxy-biphenyl-4-yl)-pyrimidine, A-f) In the case where R²* in the formula (I-A) represents an optically active alkanoyloxyalkyl group, an optically active halogen-substituted alkanoyloxyalkyl group or an optically active cyano-substituted alkanoyloxyalkyl group:

R⁷COOH
or
Compound (9) —R⁷COCl→

-continued

R¹—⟨⟩—⟨⟩—⟨N⟩—CH₂—R⁶—OCOR⁷

(I-A-f)

wherein R⁶ and R⁷ are as defined above.

Namely, an alkanoic acid or an alkanoic acid halide such as an alkanoic acid chloride is reacted with compound (9) in the preparation of A-e) to obtain the objective compound of the formula (I-A-f).

Representatives of the compounds of the formula (I-A-f) prepared according to the above process are as follows:

(S)-5-(2'-(4'-methylhexanoyloxy)ethyl)-2-(4'-propyl-biphenyl-4-yl)pyrimidine, (2'RS,6''S)-5-(6''-methyloctanoyloxy) butyl)-2-(4'-octyl-biphenyl-4-yl)-pyrimidine, (2'RS,8''S)-5-(2'-(8''-methyldecanoyloxy) pentyl)-2-(4'-propyl-biphenyl-4-yl)-pyrimidine, (2'RS,7''S)-5-(2'-(7''-methylnonanoyloxy) propyl)-2-(4'-pentyloxy-biphenyl-4-yl)-pyrimidine, A-g) In the case where R²* in the formula (I-A) represents an optically active alkoxyalkoxy group, an optically active halogen-substituted alkoxyalkoxy group or an optically active cyano-substituted alkoxyalkoxy group:

Compound (5) —A—O—R⁶—OTs (11)→

R¹—⟨⟩—⟨⟩—⟨N⟩—OR⁶OA →

(12)

-continued

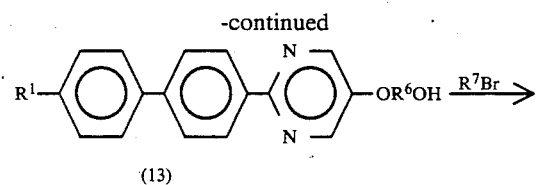

(13)

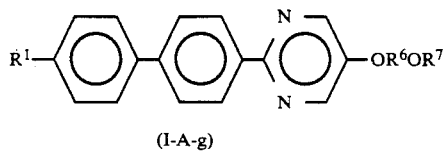

(I-A-g)

wherein R⁶, R⁷ and A are as defined above.

Namely, a compound (11) is reacted with compound (5) to obtain a compound (12), which is subjected to removal of the protecting group to obtain a compound (13), which is reacted with an alkyl halide such as an alkyl bromide, an alkyl tosylate or the like to obtain the objective compound of the formula (I-A-g).

Representatives of the compound of the formula (I-A-g) prepared according to the above process are as follows:
(S)-5-(2'-ethoxypropoxy)-2-(4'-propyl-biphenyl-4-yl)pyrimidine,
(S)-5-(2'-butoxypropoxy)-2-(4'-butyl-biphenyl-4yl)-pyrimidine,
(S)-5-(2'-pentyloxypropoxy)-2-(4'-undecyl-biphenyl-4yl)pyrimidine,
(S)-5-(2'-hexyloxypropoxy)-2-(4'-octyloxy-biphenyl-4-yl)pyrimidine,
(S)-5-(2'-hexyloxypropoxy)-2-(4'-nonyloxy-biphenyl-4-y;)pyrimidine,
(S)-5-(2'-butoxypropoxy)-2-(4'-pentyl-biphenyl-4-yl)pyrimidine,
(S)-5-(2'-hexyloxypropoxy)-2-(4'-pentyl-biphenyl-4-yl)pyrimidine.

A-h) In the case where R²* in the formula (I-A) represents an optically active alkanoyloxyalkoxy group, an optically active halogen-substituted alkanoyloxyalkoxy group or an optically active cyano-substituted alkanoyloxyalkoxy group:

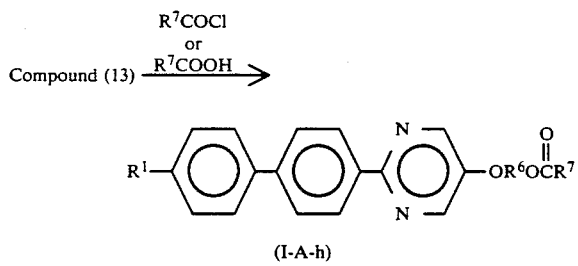

(I-A-h)

wherein R⁶ and R⁷ are as defined above.

Namely, an alkanoic acid or an alkanoic acid halide such as an alkanoic acid chloride is reacted with compound (13) to obtain the objective compound of the formula (I-A-h).

Representatives of the compound of the formula (I-A-h) prepared according to the above process are as follows:
(S)-5-(2'-valeryloxypropoxy)-2-(4'-propyl-biphenyl-4-yl)pyrimidine, (Compound No. 25)
(S)-5-(2'-pentanoyloxypropoxy)-2-(4'-propyl-biphenyl-4-yl)pyrimidine, (Compound No. 26)
(S)-5-(2'-undecanoyloxypropoxy)-2-(4'-propyl-biphenyl-4-yl)pyrimidine, (Compound No. 28)
(2'S,4"S)-5-(2'-(4'-methylhexanoyloxy) propoxy)-2-(4'-propyl-biphenyl-4-yl)pyrimidine, (Compound No. 34)
(2'S,6"S)-5-(2'-(6"-methyloctanoyloxy) propoxy)-2-(4'-propyl-biphenyl-4-yl)pyrimidine, (Compound No. 35)
(2',2"S)-5-(2'-(2"-butoxypropionloxy) propoxy)-2-(4'-propyl-biphenyl-4yl)pyrimidine, (Compound No. 38)
(2'S,2"S)-5-(2'-(2"-hexyloxypropionloxy) propoxy)-2-(4'-propyl-biphenyl-4-yl)pyrimidine, (Compound No. 39)
(2',2"S)-5-(2'-(2"-octyloxypropionyloxy) propoxy)-2-(4'-pentyl-biphenyl-4-yl)pyrimidine, (Compound No. 42)
(S)-5(2'-decanoyloxypropoxy)-2-(4'-heptly-biphenyl-4-yl)pyrimidine,
(R)-5-(2'-butyryloxypropoxy)-2-(4'-octyl-biphenyl-4-yl)pyrimidine,
(2'S,7"S)-5-(2'-(7"-methylnonanoyloxy) propoxy)-2-(4'-nonyl-biphenyl-4-yl)pyrimidine,
(R)-5-(2'-hexanoyloxypropoxy)-2-(4'-undecyl-biphenyl-4-yl)pyrimidine,
(2'S,2"S)-5-(2'-(2"-butoxypropionloxy) propoxy-2-(4'-undecyl-biphenyl-4-yl)pyrimidine,
(2'S,2"S)-5-(2'-(2"-hexyloxypropionyloxy) propoxy)-2-(4'-butoxy-biphenyl-4-yl)pyrimidine,
(R)-5-(2'-valeryloxypropoxy)-2-(4'-pentyloxy-biphenyl-4-yl)pyrimidine,
(S)-5-(2'-hexanoyloxypropoxy)-2-(4'-hexyloxy-biphenyl-4-yl)pyrimidine,
(2'S,2"S)-5-(2'-(2"-hexyloxypropionyloxy) propoxy)-2-(4'-hexyloxy-biphenyl-4-yl)pyrimidine, (Compound No. 47)
(2'S,2"S)-5-(2'-(4"-butoxypropionyloxy) propoxy)-2-(4'-heptyloxy-biphenyl-4-yl)pyrimidine,
(S)-5-(2'-butyryloxypropoxy)-2-(4'-octyloxy-biphenyl-4-pyrimidine,
(2'S,2"S)-5-(2'-(2"-hexyloxypropionyloxy) propoxy)-2-(4'-nonyloxy-biphenyl-4-yl)pyrimidine,
(S)-5-(2'-hexanoyloxypropoxy)-2-(4'-undecyloxy-biphenyl-4-yl)pyrimidine, (2'S, 2"S)-5-(2'-(2"-heptyloxypropionyloxy)propoxy)-2-(4'-undecyloxybiphenyl-4-yl)pyrimidine,
(S)-5-(2'-octanoyloxypropoxy)-2-(4'-undecyloxy-biphenyl-4-yl)pyrimidine,
(S)-5-(2'-(4"-methylpentanoyloxy)propoxy)-2-(4'-propyl-biphenyl-4-yl)-pyrimidine, (Compound No. 33)
(S)-5-(2'-nonanoyloxypropoxy)-2-(4'-pentyl-biphenyl-4-yl)pyrimidine,
(S)-5-(2'-octanoyloxypropoxy)-2-(4'-dodecyl-biphenyl-4-yl)pyrimidine,
(2'S, 2"S)-5-(2'-(2"-hexyloxypropionyloxy)propoxy)-2-(4'-butoxy-biphenyl-4-yl)pyrimidine,
(S)-5-(2'-hexanoyloxypropoxy)-2-(4'-propyl-biphenyl-4-yl)pyrimidine, (Compound No. 27)
(S)-5-(2'-valeryloxypropoxy)-2-(4'-hexyl-biphenyl-4-yl)pyrimidine, (Compound No. 29)
(2'S, 2"S)-5-(2'-(2"-pentyloxypropionyloxy)propoxy)-2-(4'-hexyl-biphenyl-4-yl)pyrimidine, (Compound No. 43)
(2'S, 2"S)-5-(2'-(2"-hexyloxypropionyloxy)propoxy)-2-(4'-hexylpropylbiphenyl-4-yl)pyrimidine, (Compound No. 44).

A-i) In the case where R²* in the formula (I-A) represents an optically active alkoxyalkanoyloxy group, an optically active halogen-substituted alkoxyalkanoyloxy group or an optically active cyano-substituted alkoxyalkanoyloxy group:

Compound (5) $\xrightarrow{R^7OR^6COOH\ (14)}$

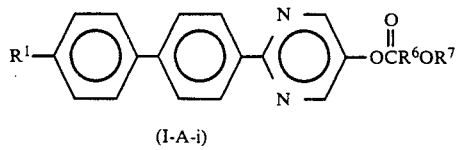

(I-A-i)

wherein $R^6$ and $R^7$ are as defined above.

Namely, a compound (14) is reacted with compound (5) to obtain the objective compound of the formula (I-A-i).

Representatives of the compounds of the formula (I-A-i) prepared according to the above process are as follows:

(S)-5-(2'-hexyloxypropionyloxy)-2-(4'-propyl-biphenyl-4-yl)pyrimidine, (Compound No. 21)
(R)-5-(2'-butoxypropionyloxy)-2-(4'-hexyl-biphenyl-4-yl)pyrimidine,
(S)-5-(2'-butoxypropionyloxy)-2-(4'-heptyl-biphenyl-4-yl)pyrimidine,
(R)-5-(2'-pentyloxypropionyloxy)-2-(4'-heptyl-biphenyl-4-yl)pyrimidine,
(S)-5-(2'-hexyloxypropionyloxy)-2-(4'-heptyl-biphenyl-4-yl)pyrimidine,
(R)-5-(2'-butoxypropionyloxy)-2-(4'-octyl-biphenyl-4-yl)pyrimidine,
(S)-5-(2'-pentyloxypropionyloxy)-2-(4'-octyl-biphenyl-4-yl)pyrimidine,
(R)-5-(2'-hexyloxypropionyloxy)-2-(4'-octyl-biphenyl-4-yl)pyrimidine,
(S)-5-(2'-pentyloxypropionyloxy)-2-(4'-hexyloxy-biphenyl-4-yl)pyrimidine, (Compound No. 24)
(R)-5-(2'-hexyloxypropionyloxy)-2-(4'-octyloxy-biphenyl-4-yl)pyrimidine,
(S)-5-(2'-butoxypropionyloxy)-2-(4'-hexyl-biphenyl-4-yl)pyrimidine, (Compound No. 22)
(S)-5-(2'-pentyloxypropionyloxy)-2-(4'-hexyl-biphenyl-4-yl)pyrimidine, (Compound No. 23).

A-j) In the case where $R^{2*}$ in the formula (I-A) represents an optically active alkoxycarbonyl group, an optically active halogen-substituted alkoxycarbonyl group or an optically active cyano-substituted alkoxycarbonyl group:

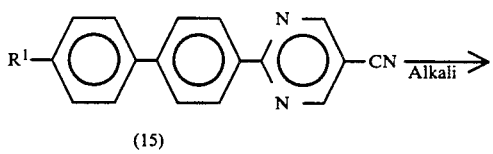

(15)

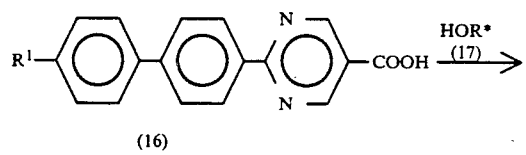

(16)

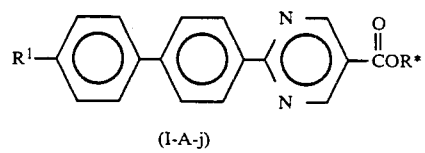

(I-A-j)

wherein R* represents the above-mentioned optically active alkyl group or optically active halogen-substituted alkyl group.

Namely, a compound (15) is hydrolyzed into compound (16), which is reacted with a compound (17) to obtain the compound of the formula (I-A-j).

Representatives of the compounds of the formula (I-A-j) prepared according to the above process are as follows:

(R)-5-(4'-methylhexyloxycarbonyl)-2-(4'-ethyl-biphenyl-4-yl)pyrimidine,
(R)-5-(5'-methylheptyloxycarbonyl)-2-(4'-propyl-biphenyl-4-yl)pyrimidine,
(S)-5-(6'-methyloctyloxycarbonyl)-2-(4'-pentyl-biphenyl-4-yl)pyrimidine,
(S)-5-(1'-methyloctyloxycarbonyl)-2-(4'-octyloxy-biphenyl-4-yl)pyrimidine, A-k) In the case where $R^{2*}$ in the formula (I-A) represents an optically active alkoxyalkoxycarbonyl group, an optically active halogen-substituted akloxyalkoxycarbonyl group or an optically active cyano-substituted alkoxyalkoxycarbonyl group:

Compound (16) $\xrightarrow{HOR^6OR^7\ (18)}$

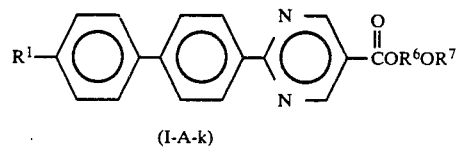

(I-A-k)

wherein $R^6$ and $R^7$ are as defined above.

Namely, a compound (18) is reacted with compound (16) to obtain the objective compound of the formula (I-A-k).

Representatives of the compounds of the formula (I-A-k) prepared according to the above process are as follows:

(R)-5-(2'-butoxypropoxycarbonyl)-2-(4'-hexyl-biphenyl-4-yl)pyrimidine,
(R)-5-(2'-pentyloxypropoxycarbonyl)-2-(4'-hexyl-biphenyl-4-yl)pyrimidine,
(2'S, 6''S)-5-(2'-(6''-methyloctyloxy)propoxycarbonyl)-2-(4'-octyl-biphenyl-4-yl)pyrimidine,
(2'S, 6''S)-5-(2'-(6''-methyloctyloxy)propoxycarbonyl)-2-(4'-nonyl-biphenyl-4-yl)pyrimidine.

B)

B-a) In the case where $R^{1*}$ in the formula (I-B) represents an optically active alkyl group, an optically active halogen-substituted alkyl group or an optically active cyano-substituted alkyl group:

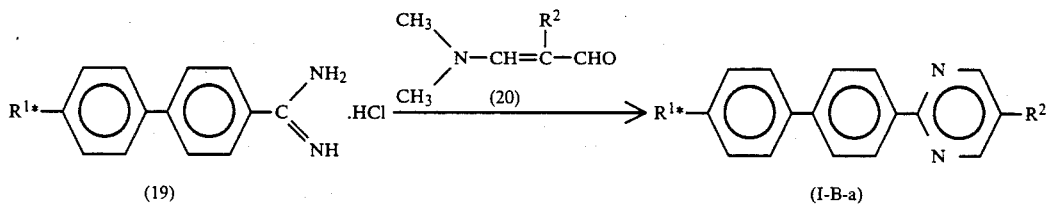

wherein R[1]* represents an optically active alkyl group, an optically active halogen-substituted alkyl group or an optically active cyano-substituted alkyl group.

Namely, a compound (20) is reacted with compound (19) under a basic condition to obtain a compound (I-B-a).

Representatives of the compounds of (I-B-a) prepared according to the above process are as follows:
(S)-5-hexyl-2-(4'-(2''-methylbutyl)-biphenyl-4-yl)-pyrimidine,
(S)-5-hexyl-2-(4'-(4''-methylhexyl)-biphenyl-4-yl)-pyrimidine,
(R)-5-heptyl-2-(4'-(1''-methyloctyl)-biphenyl-4-yl)-pyrimidine,
(R)-5-heptyl-2-(4'-(2''-chlorobutyl)-biphenyl-4-yl)-pyrimidine,
(S)-5-octyl-2-(4'-(3''-fluoroheptyl)-biphenyl-4-yl)-pyrimidine,
(S)-5-octyl-2-(4'-(2''-cyanopentyl)-biphenyl-4-yl)-pyrimidine,
(R)-5-pentyloxy-2-(4'-(1''-methylhexyl)-biphenyl-4-yl)-pyrimidine,
(S)-5-pentyloxy-2-(b  4'-(2''-methylnonyl)-biphenyl-4-yl)-pyrimidine,
(S)-5-nonyloxy-2-(4'-(2''-chlorodecyl)-biphenyl-4-yl)-pyrimidine,
(S)-5-nonyloxy-2-(4'-(2''-fluorobutyl)-biphenyl-4-yl)-pyrimidine.

B-b) In the case where R[1]* in the formula (I-B) represents an optically active alkoxy group, an optically active halogen-substituted alkoxy group or an optically active cyano-substituted alkoxy group:

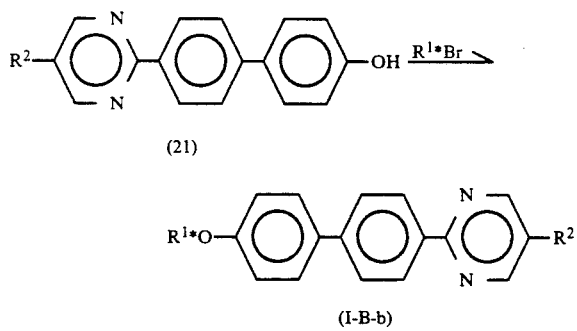

wherein R[1]* represents the above-mentioned optically active alkyl group, optically active halogen-substituted alkyl group or optically active cyano-substituted alkyl group.

Namely, an alkyl halide such as an alkyl bromide, an alkyl tosylate, or the like is reacted with compound (21) under a basic condition to obtain a compound of the formula (I-B-b).

Representatives of the compounds of the formula (I-B-b) prepared according to the above process are as follows:
(S)-5-pentyl-2-(4'-(2''-methylbutoxy)-biphenyl-4-yl)-pyrimidine,
(S)-5-pentyl-2-(4'-(2''-chlorobutoxy)-biphenyl-4-yl)-pyrimidine,
(R)-5-heptyl-2-(4'-(1''-methyloctyloxy)-biphenyl-4-yl)-pyrimidine,
(R)-5-heptyl-2-(4'-(1''-methylheptyloxy)-biphenyl-4-yl)-pyrimidine,
(S)-5-heptyl-2-(4'-(8''-methyldecyloxy)-biphenyl-4-yl)-pyrimidine, (Compound No. 49)
(R)-5-hexyloxy-2-(4'-(2''-cyanobutyloxy)-biphenyl-4-yl)-pyrimidine,
(S)-5-hexyloxy-2-(4'-(3''-fluorononyloxy)-biphenyl-4-yl)-pyrimidine,
(S)-5-heptyloxy-2-(4'(2''-fluorobutoxy)-biphenyl-4-yl)-pyrimidine,
(S)-5-heptyl-2-(4'-(2''-fluorooctyloxy)-biphenyl-4-yl)-pyrimidine, (Compound No. 53)
(S)-5-heptyloxy-2-(4'-(6''-methyloctyloxy)-biphenyl-4-yl)-pyrimidine,
(S)-5-octyloxy-2-(4'-(7''-methylnonyloxy)-biphenyl-4-yl)-pyrimidine,
(S)-5-octyloxy-2-(4'-(5''-chloroheptyloxy)-biphenyl-4-yl)-pyrimidine
(S)-5-octyl-2-(4'-(1''-methylheptyloxy)-biphenyl-4-yl)-pyrimidine (Compound No. 48)

B-c) In the case where R[1]* in the formula (I-B) represents an optically active alkanoyloxy group, an optically active halogen-substituted alkanoyloxy group or an optically active cyano-substituted alkanoyloxy group:

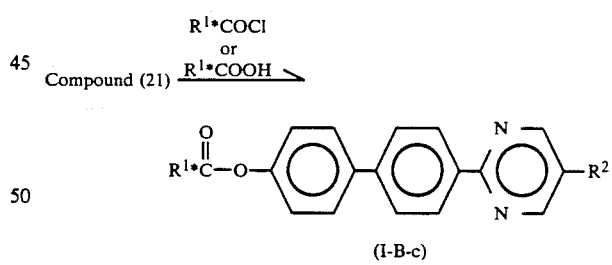

wherein R[1]* is as defined above.

Namely, various alkanoic acids or various alkanoic acid chlorides are reacted with compound (21) to obtain a compound of the formula (I-B-c).

Representatives of the compounds of the formula (I-B-c) prepared according to the above process are as follows:
(S)-5-butyl-2-(4'-(3''-methylvaleryloxy)-biphenyl-4-yl)-pyrimidine,
(2''S, 3''S)-5-butyl-2-(4'-(2''-chloro-3''-methylvaleryloxy)-biphenyl-4-yl)-pyrimidine,
(R)-5-octyl-2-(4'-(3''-fluorooctanoyloxy)-biphenyl-4-yl)-pyrimidine,
(S)-5-octyl-2-(4'-(2''-cyanohexanoyloxy)-biphenyl-4-yl)-pyrimidine, (S)-5-pentyl-2-(4'-(2''-methyloctanoyloxy)-biphenyl-4-yl)-pyrimidine,
(S)-5-pentyloxy-2-(4'-(2''-cyanodecanoyloxy)-biphenyl-4-yl)-pyrimidine,
(S)-5-octyloxy-2-(4'-(3''-fluorovaleryloxy)-biphenyl-4-yl)-pyrimidine,
(S)-5-octyloxy-2-(4'-(4''-methylheptanoyloxy)-biphenyl-4-yl)-pyrimidine,
(S)-5-dodecyloxy-2-(4'-(5''-methyldecanoyloxy)-biphenyl-4-yl)-pyrimidine,
(S)-5-dodecyloxy-2-(4'-(5''-methylundecanoyloxy)-biphenyl-4-yl)-pyrimidine.

B-d) In the case where R¹* of the formula (I-B) represents an optically active alkoxycarbonyloxy group, an optically active halogen-substituted alkoxycarbonyloxy group or an optically active cyano-substituted alkoxycarbonyloxy group:

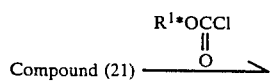

Representatives of the compounds of the formula (I-B-d) prepared according to the above process are as follows:

(S)-5-hexyl-2-(4'-(2''-methylbutoxycarbonyloxy)-biphenyl-4-yl)-pyridimidine,
(R)-5-hexyl-2-(4'-(1''-methylheptyloxycarbonyloxy)-biphenyl-4-yl)-pyrimidine,
(S)-5-heptyl-2-(4'-(5''-methylheptyloxycarbonyloxy)-biphenyl-4-yl)-pyrimidine,
(S)-5-heptyl-2-(4'-(4''-methylhexyloxycarbonyloxy)-biphenyl-4-yl)-pyrimidine,
(S)-5-nonyloxy-2-(4'-(2''-fluorobutoxycarbonyloxy)-biphenyl-4-yl)-pyrimidine,
(S)-5-nonyloxy-2-(4'-(3''-chloropentyloxycarbonyloxy)-biphenyl-4-yl)-pyrimidine,
(R)-5-decyloxy-2-(4'-(1''-methylheptyloxycarbonyloxy)-biphenyl-4-yl)-pyrimidine,
(S)-5-decyloxy-2-(4'-(1''-fluorobutoxycarbonyloxy)-biphenyl-4-yl)-pyrimidine.

B-e) In the case where R¹* of the formula (I-B) represents an optically active alkoxyalkyl group, an optically active halogen-substituted alkoxyalkyl group or an optically active cyano-substituted alkoxyalkyl group:

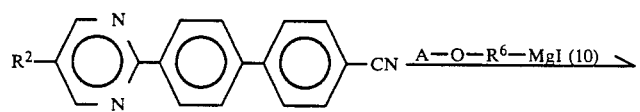
(22)

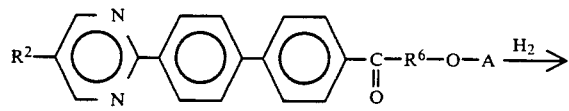
(23)

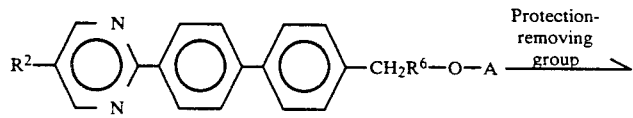
(24)

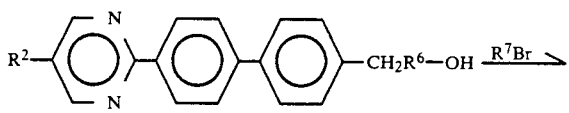
(25)

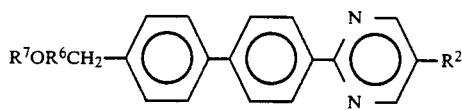
(I-B-e)

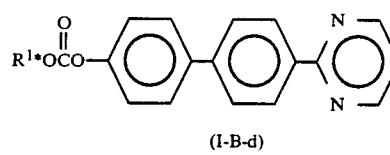
(I-B-d)

wherein R¹* is as defined above.

Namely, various alkyl chloroformates are reacted with compound (21) to obtain a compound of the formula (I-B-d).

wherein R⁶ and R⁷ are as defined above.

Namely, a Grignard reagent expressed by the formula (10) is reacted with the compound (22) to obtain a compound (23), which is then reduced into a compound (24), followed by subjecting this compound to removal of the protecting group to obtain a compound (25), reacting therewith an alkyl halide such as alkyl bromide, an alkyl tosylate or the like to obtain a compound of the formula (I-B-e).

Representatives of the compounds of the formula (I-B-e) prepared according to the above process are as follows:
(R)-5-heptyl-2-(4'-(2"-(12''''-methyloctyloxy)ethyl)-biphenyl-4-yl)-pyrimidine,
(R)-5-heptyl-2-(4'-(2"-(2''''-chloro-3''''-methylpentyloxy)ethyl)-biphenyl-4-yl)-pyrimidine,
(S)-5-octyl-2-(4'-(2"-methyl-3"-heptyloxy)propyl)-biphenyl-4-yl)-pyrimidine,
(S)-5-octyl-2-(4'-(2"-methyl-3"-(2''''-fluoropentyloxy)propyl)-biphenyl-4-yl)-pyrimidine,
(S)-5-nonyl-2-(4'-(2"-(2''''-chlorobutoxy)propyl)-biphenyl-4-yl)-pyrimidine,
(R)-5-nonyl-2-(4'-(2"-nonyloxypropyl)-biphenyl-4-yl)-pyrimidine,
(R)-5-hexyloxy-2-(4'-(2"-pentyloxypropyl)-biphenyl-4-yl)-pyrimidine,
(S)-5-hexyloxy-2(4'-(2"-decyloxypropyl)-biphenyl-4-yl)-pyrimidine,
(R)-5-octyloxy-2-(4'-(2"-propoxyethyl)-biphenyl-4-yl)-pyrimidine,
(R)-5-octyloxy-2-(4'-(2"'-methylbutoxy)ethyl)-biphenyl-4-yl)-pyrimidine.

B-f) In the case where R¹* of the formula (I-B) represents an optically active alkanoyloxyalkyl group, an optically active halogen-substituted alkanoyloxyalkyl group or an optically active cyano-substituted alkanoyloxyalkyl group:

Compound (25) $\xrightarrow{\text{R}^7\text{COOH or R}^7\text{COCl}}$

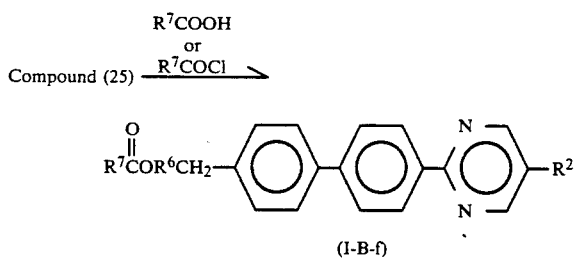

(I-B-f)

wherein R⁶ and R⁷ are as defined above.

Namely, an alkanoic acid or an alkanoic acid halide such as an alkanoic acid chloride is reacted with compound (25) in the preparation of (B-e) to obtain a compound of the formula (I-B-f).

Representatives of the compounds of the formula (I-B-f) prepared according to the above process are as follows:
(R)-5-hexyl-2-(4'-(2"-(2"-butyryloxy)ethyl-biphenyl-4-yl)-pyrimidine,
(S)-5-hexyl-2-(4'-(2"-(2''''-methylbutyryloxy)ethyl)-biphenyl-4-yl)-pyrimidine,
(R)-5-octyl-2-(4'-(2"-hexanoyloxyethyl)-biphenyl-4-yl)-pyrimidine,
(S)-5-octyl-2-(4'-(2"-nonanoyloxypropyl)-biphenyl-4-yl)-pyrimidine,
(R)-5-decyl-2-(4'-(2"-propionyloxypropyl)-biphenyl-4-yl)-pyrimidine,
(2"S,3'''R)-5-decyl-2-(4'-(2"-(3''''-methylvaleryloxy)propyl)-biphenyl-4-yl-pyrimidine,
(R)-5-butoxy-2-(4'-(2"-methyl-3"-hexanoyloxypropyl)-biphenyl-4-yl)-pyrimidine,
(R)-5-butoxy-2-(4'-(2"-methyl-3"-(3''''-fluoropentanoyloxy)ethyl)-biphenyl-4-yl)-pyrimidine,
(R)-5-heptyloxy-2-(4'-(2"-(2''''-methyloctanoyloxy)ethyl)-biphenyl-4-yl)-pyrimidine,
(2'''S, 3"S)-5-hexyl-2-(4'-(3"-(2''''-chloro-3''''-methylvaleryloxy)propyl)-biphenyl-4-yl)-pyrimidine.

B-g) In the case where R¹* of the formula (I-B) represents an optically active alkoxyalkoxy group, an optically active halogen-substituted alkoxyalkoxy group or an optically active cyano-substituted alkoxyalkoxy group:

Compound (21) $\xrightarrow{\text{A}-\text{O}-\text{R}^6-\text{OTs (11)}}$

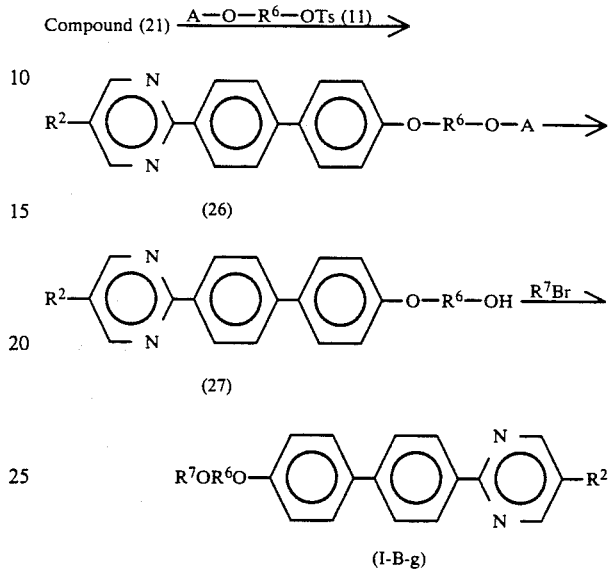

wherein R⁶, R⁷ and A are as defined above.

Namely, compound (11) is reacted with compound (21) to obtain compound (26), which is then subjected to removal of the protecting group to obtain compound (27), which is then reacted with an alkyl halide such as an alkyl bromide, an alkyl tosylate, etc. to obtain the objective compound of the formula (I-B-g).

Representatives of the compounds of the formula (I-B-g) prepared according to the above process are as follows:
(R)-5-pentyl-2-(4'-(2"-(1''''-methyloctyloxy)ethoxy)-biphenyl-4-yl)-pyrimidine,
(R)-5-pentyl-2-(4'-(3"-(2''''-chloro-3''''-methylpentyloxy)ethoxy)-biphenyl-4-yl)-pyrimidine,
(R)-5-heptyl-2-(4'-(2"-methyl-3"-octyloxypropoxy)-biphenyl-4-yl)-pyrimidine,
(R)-5-heptyl-2-(4'-(2"-methyl-3-(2''''-fluorobutoxy)propoxy)-biphenyl-4-yl)-pyrimidine,
(R)-5-hexyloxy-2-(4'-(2"-ethoxypropoxy)-biphenyl-4-yl)-pyrimidine,
(R)-5-hexyloxy-2-(4'-(2"-chlorobutoxy)propoxy)-biphenyl-4-yl)-pyrimidine,
(R)-5-heptyloxy-2-(4'-(2"-methoxypropoxy)-biphenyl-4-yl)-pyrimidine,
(R)-5-heptyloxy-2-(4'-(2"-hexyloxypropoxy)-biphenyl-4-yl)-pyrimidine,
(R)-5-octyloxy-2-(4'-(2"-(2''''-cyanobutoxy)ethyloxy)-biphenyl-4-yl)-pyrimidine.

B-h) In the case where R¹* of the formula (I-B) represents an optically active alkanoyloxyalkoxy group, an optically active halogen-substituted alkanoyloxyalkoxy group or an optically active cyano-substituted alkanoyloxyalkoxy group:

Compound (27) $\xrightarrow{\text{R}^7\text{COOH or R}^7\text{COCl}}$

-continued

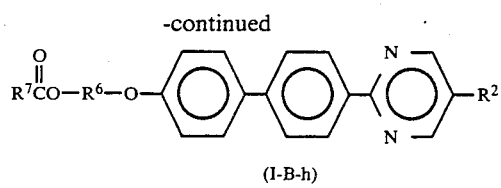
(I-B-h)

wherein R⁶ and R⁷ are as defined above.

Namely, an alkanoic acid or an alkanoic acid halide such as an alkanoic acid chloride is reacted with compound (27) to obtain a compound of the formula (I-B-h).

Representatives of the compounds of the formula (I-B-h) prepared according to the above process are as follows:
(R)-5-butyl-2-(4'-(2''-valeryloxypropoxy)-biphenyl-4-yl)-pyrimidine,
(R)-5-butyl-2-(4'-(2''-(3''''-methylvaleryloxy)propoxy)-biphenyl-4-yl)-pyrimidine,
(2''S,2'''S)-5-hexyl-2-(4'-(2''-(2'''-methylbutyryloxy)-propoxy)-biphenyl-4-yl)-pyrimidine,
(2''S,2'''S)-5-hexyl-2-(4'-(2''-(2'''-butoxypropionyloxy)-propoxy)-biphenyl-4-yl)-pyrimidine, (Compound No. 51)
(S)-5-octyl-2-(4'-(2''-valeryloxypropoxy)-biphenyl-4-yl)-pyrimidine, (Compound No. 50)
(2''S,2'''S)-5-octyl-2-(4'-(2''-(2'''-butoxypropionyloxy)-propoxy)-biphenyl)-4-yl)-pyrimidine, (Compound No. 52)
(R)-5-decyl-2-(4'-(2''-hexanoyloxypropoxy)-biphenyl-4yl)-pyrimidine,
(2''S,3'''S)-5-decyl-2-(4'-(2''-(3''''-fluorovaleryloxy)-propoxy)-biphenyl-4-yl)-pyrimidine,
(2''S,2'''R)-5-pentyloxy-2-(4'-(2''-(2'''-chlorovaleryloxy)-propoxy)-biphenyl-4-yl)-pyrimidine,
(2''S,2'''S)-5-pentyloxy-2-(4'-(2''-(2'''-propoxypropionyloxy)-propoxy)-biphenyl-4-yl)-pyrimidine,
(R)-5-hexyl-2-(4'-(2''-butyryloxypropoxy)-biphenyl-4-yl)-pyrimidine,
(R)-5-hexyloxy-2-(4'-(2''-(2''''-pentyloxypropionyloxy)-propoxy)-biphenyl-4-yl)-pyrimidine,
(2''S,2'''S)-5-heptyloxy-2-(4'-(2''-(2'''-methyloctanoyloxy)propoxy)-biphenyl-4-yl)-pyrimidine,
(R)-5-heptyloxy-2-(4'-(2''-heptanoyloxypropoxy)-biphenyl-4-yl)-pyrimidine,
(R)-5-octyloxy-2-(4'-(2''-heptanoyloxypropoxy)-biphenyl-4-yl)-pyrimidine,
(R)-5-octyloxy-2-(4'-(2''-octanoyloxypropoxy)-biphenyl-4-yl)-pyrimidine.

B-i) In the case where R¹* of the formula (I-B) represents an optically active alkoxyalkanoyloxy group, an optically active halogen-substituted alkoxyalkanoyloxy group or an optically active cyano-substituted alkoxyalkanoyloxy group:

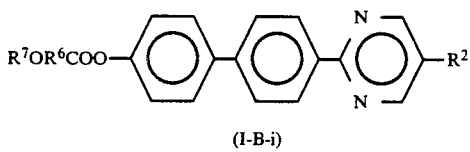
(I-B-i)

wherein R⁶ and R⁷ are as defined above.

Namely, compound (14) is reacted with compound (21) to obtain the objective compound of the formula (I-B-i).

Representatives of the compounds of the formula (I-B-i) prepared according to the above process are as follows:
(R)-5-hexyl-2-(4'-(3''-(2''''-methylpentyloxy)propionyloxy)-biphenyl-4-yl)-pyrimidine,
(R)-5-hexyl-2-(4'-(3''-(2''''-methylhexyloxy)propionyloxy)-biphenyl-4-yl)-pyrimidine,
(R)-5-heptyl-2-(4'-(3''-hexyloxy)butyryloxy)-biphenyl-4-yl)-pyrimidine,
(R)-5-heptyl-2-(4'-(3''-(2''''-chlorobutoxy)butyryloxy-biphenyl-4-yl)-pyrimidine,
(R)-5-octyl-2-(4'-(3''-(3''''-fluoropentyloxy)propionyloxy)-biphenyl-4-yl)-pyrimidine,
(R)-5-nonyloxy-2-(4'-(2''-methyl-3''-hexyloxy)propionyloxy)-biphenyl-4-yl)-pyrimidine,
(R)-5-nonyloxy-2-(4'-(2''-methyl-3''-(2''''-cyanobutoxy)-propionyloxy)-biphenyl-4-yl)-pyrimidine,
(R)-5-decyloxy-2-(4'-(2''-methyl-3''-(4''''-methylhexyloxy)propionyloxy)-biphenyl-4-yl)-pyrimidine,
(R)-5-decyloxy-2-(4'-(2''-methyl-3''-(4''''-methylhexyloxy)propionyloxy)-biphenyl-4-yl)-pyrimidine, B-j) In the case where R¹* of the formula (I-B) represents an optically active alkoxycarbonyl group, an optically active halogen-substituted alkoxycarbonyl group or an optically active cyano-substituted alkoxycarbonyl group:

Compound (22) $\xrightarrow{\text{Alkali}}$ $R^2-\underset{N}{\overset{N}{\bigcirc}}-\bigcirc-\bigcirc-COOH \xrightarrow{HOR^*}_{(17)}$ (28)

$R^*OC-\bigcirc-\bigcirc-\underset{N}{\overset{N}{\bigcirc}}-R^2$ (I-B-j)

wherein R* is as defined above.

Namely, compound (22) is hydrolyzed into compound (28), which is then reacted with compound (17) to obtain a compound of the formula (I-B-j).

Representatives of the compounds of the formula (I-B-j) prepared according to the above process are as follows:
(S)-5-pentyl-2-(4'-(2''-methylbutoxycarbonyl)-biphenyl-4-yl)-pyrimidine,
(R)-5-pentyl-2-(4'-(1''-methylheptyloxycarbonyl)-biphenyl-4-yl)-pyrimidine,
(R)-5-nonyl-2-(4'-(2''-methyldecyloxycarbonyl)-biphenyl-4-yl)-pyrimidine,
(R)-5-nonyl-2-(4'-(2''-methylundecyloxycarbonyl)-biphenyl-4-yl)-pyrimidine,
(R)-5-5-hexyl-2-(4'-(2''-chlorononyloxycarbonyl)-biphenyl-4-yl)-pyrimidine,
(S)-5-hexyloxy-2-(4'-(5''-methylheptyloxycarbonyl)-biphenyl-4-yl)-pyrimidine,
(R)-5-nonyloxy-2-(4'-(2''-fluoropentyloxycarbonyl)-biphenyl-4-yl)-pyrimidine,
(R)-5-nonyloxy-2-(4'-(3''-cyanoheptyloxycarbonyl)-biphenyl-4-yl)-pyrimidine,
(R)-5-undecyloxy-2-(4'-(2''-fluorohexyloxycarbonyl)-biphenyl-4-yl)-pyrimidine, (R)-5-undecyloxy-2-(4'-(1"-cyanobutoxycarbonyl)-biphenyl-4-yl)-pyrimidine.

B-k) In the case where $R^{1*}$ of the formula (I-B) represents an optically active alkoxyalkoxycarbonyl group, an optically active halogen-substituted alkoxyalkoxycarbonyl group or an optically active cyano-substituted alkoxyalkoxycarbonyl group:

Compound (28) $\xrightarrow{HOR^6OR^7 \text{ (18)}}$ $$R^7OR^6OC-\bigcirc-\bigcirc-\bigcirc-R^2$$

(I-B-k)

wherein $R^6$ and $R^7$ are as defined above.

Namely, compound (18) is reacted with compound (28) to obtain the objective compound of the formula (I-B-k).

Representatives of the compounds of the formula (I-B-k) prepared according to the above process are as follows:

(S)-5-heptyl-2-(4'-(2"-(2'''-fluoropentyloxy)ethoxycarbonyl)-biphenyl-4-yl)pyrimidine,
(S)-5-heptyl-2-(4'-(2"-(1'''-methylhexyloxy)ethoxycarbonyl)-biphenyl-4-yl)-pyrimidine,
(S)-5-octyl-2-(4'-(2"-(2'''-fluoropentyloxy)ethoxycarbonyl)-biphenyl-4-yl)-pyrimidine,
(S)-5-hexyloxy-2-(4'-(2"-cyano-2"-(2'''-methylpentyloxy)ethoxycarbonyl)-biphenyl-4-yl)-pyrimidine,
(S)-5-octyloxy-2-(4'-(2"-butoxypropoxy)propoxycarbonyl)-biphenyl-4-yl)-pyrimidine,
(S)-5-octyloxy-2-(4'-(2"-(2'''-cyanobutoxy)propoxycarbonyl)-biphenyl-4-yl)-pyrimidine,
(S)-5-nonyloxy-2-(4'-(1"-methyl-2"-pentyloxy)ethoxycarbonyl)-biphenyl-4-yl)-pyrimidine,
(S)-5-nonyloxy-2-(4'-(1"-methyl-2"-(4'''-methylhexyloxy)ethoxycarbonyl)-biphenyl-4-yl)-pyrimidine,
(S)-5-heptyl-2-(4'-(2"-(2'''-fluoropentyloxy)ethoxycarbonyl)-biphenyl-4-yl)-pyrimidine,
(S)-5-heptyl-2-(4'-(2"-(2'''-fluoropentyloxy)ethoxycarbonyl)-biphenyl-4-yl)-pyrimidine.

The optically active compound of the present invention will be described in more detail by way of Examples.

EXAMPLE 1

Preparation of (S)-5-(2'-valeryloxypropoxy)-2-(4'-propyl-biphenyl-4-yl)pyrimidine (a compound of the formula (I) wherein $R^1=-C_3H_7$ and $R^2=$ $$-OCH_2\overset{*}{C}H\overset{CH_3}{\underset{|}{}}O\overset{O}{\underset{\|}{C}}C_4H_9;$$

compound No. 25)

A solution of (S)-2-tetrahydropyranyloxy-1-(p-toluenesulfonyloxy)-propane (192 g, 0.62 mol) prepared in the same manner as in a process described in Example 1 of the specification of Japanese patent application No. Sho 61-133269/1986 in tetrahydrofuran (hereinafter abbreviated to THF) (2,000 ml) was added to a mixture of 60% sodium hydride (31 g, 0.62 mol), 5-hydroxy-2-(4'-propyl-4"-biphenylyl)pyrimidine (150 g, 0.52 mol) and THF (1,200 ml), followed by agitating the resulting mixture at 60° C. for 4 hours, allowing it to cool down to room temperature, adding toluene, washing the resulting organic layer with an alkali and then with water, concentrating it, dissolving the concentrate in ethanol (2,000 ml), adding 6N-hydrochloric acid (40 ml), agitating the mixture at 60° C. for one hour, allowing it to cool down to room temperature, collecting deposited crystals and recrystallizing them from ethyl acetate (1,000 ml) to obtain (S)-5-(2'-hydroxypropyloxy)-2-(4'-propyl-biphenyl-4-yl)-pyrimidine (122 g), which was a liquid crystal and had phase transition points of C-Ch point 161.0° C. and Ch-I point 208.1° C. This (S)-5-(2'-hydroxypropoxy)-2-(4'-propyl-biphenyl-4-yl)pyrimidine (10 g, 0.029 mol), n-pentanoic acid (4.4 g, 0.044 mol), dicyclohexylcarbodiimide (hereinafter abbreviated to DCC) (24 g, 0.12 mol) and dimethylaminopyridine (hereinafter abbreviated to DMAP) (3.9 g) were dissolved in dichloromethane (150 ml), followed by agitating the solution at room temperature for 2 hours, filtering off deposited crystals, washing the filtrate with an alkali and then with water, concentrating it and twice recrystallizing the residue from ethanol (200 ml) to obtain (S)-5-(2'-valeryloxypropoxy)-2-(4'-propyl-biphenyl-4-yl)-pyrimidine (9.8 g).

This product was a liquid crystal and exhibited the following phase transition points (also see Table 1):

$$C \xrightarrow{98.5° C.} I$$
$$\searrow \nearrow 70.0° C.$$
$$Ch$$

EXAMPLE 2

Preparation of (S)-5-(6'-methyloctyloxy)-2-(4'-propyl-biphenyl-4-yl)pyrimidine (a compound of the formula (I) wherein $R^1=-C_3H_7$ and $R^2=$ $$-O(CH_2)_5\overset{*}{C}H\overset{CH_3}{\underset{|}{}}C_2H_5;$$

compound No. 5)

5-Hydroxy-2(4'-propyl-biphenyl-4-yl)pyrimidine (10 g, 0.034 mol) was dissolved in ethanol (100 ml), followed by adding KOH (2.1 g, 0.037 mol), refluxing the mixture, dropwise adding (S)-6-methyloctyl bromide (7.7 g, 0.037 mol) over about 15 minutes, further refluxing the mixture for 5 hours, distilling off ethanol (80 ml), dissolving the residue in toluene (100 ml), transferring the solution into a separating funnel, sufficiently washing it with a 2N-NaOH aqueous solution, washing it with water until the washing water became neutral, drying the resulting organic layer over anhydrous magnesium sulfate, distilling off toluene and recrystallizing the residue from ethanol (200 ml) to obtain (S)-5-(6'-methyloctyloxy)-2(4'-propylbiphenyl-4-yl)pyrimidine (8.9 g). This product was a liquid crystal and exhibited the following phase transition points (also see Table 1):

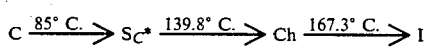

EXAMPLE 3

Preparation of (S)-5-(6'-methyloctanoyloxy)-2-(4'-propyl-biphenyl-4-yl)pyrimidine
(a compound of the formula (I) wherein $R^1 = -C_3H_7$ and $R^2 =$

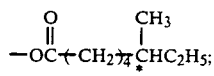

compound No. 17)

5-Hydroxy-2(4'-propyl-biphenyl-4-yl)pyrimidine (10 g, 0.034 mol) was dissolved in dichloromethane (100 ml), followed by adding (S)-6-methyloctanoic acid (7.9 g, 0.05 mol), DCC (20.6 g, 0.1 mol) and DMAP (3.3 g), agitating the mixture at room temperature for 2 hours, filtering off deposited crystals, washing the filtrate with 6N-HCl, then with 2N-NaOH and further with water until the washing water became neutral, drying the organic layer over anhydrous magnesium sulfate, distilling off dichloromethane and recrystallizing the residue from ethanol (150 ml) to obtain (S)-5-(6'-methyloctanoyloxy)-2-(4'-propylbiphenyl-4-yl)pyrimidine (9.9 g). This product was a liquid crystal and exhibited the following phase transition points (see also Table 1):

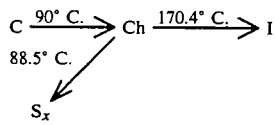

EXAMPLE 4

Preparation of (S)-5-(2'-methylbutyl)-2-(4'-pentyl-biphenyl-4-yl)pyrimidine (a compound of the formula (I) wherein $R^1 = -C_5H_{11}-$ and $R^2 =$

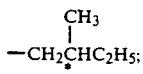

compound No. 1)

Sodium (57.5 g, 2.5 mols) was added to ethanol (1 l) to prepare sodium methoxide, followed by adding (S)-2-methylbutyl bromide (317 g, 2.1 mols) and diethyl malonate 400 g, 2.5 mols), refluxing the mixture for 5 hours and distilling off ethanol to obtain oily diethyl (S)-2-methylbutylmalonate.

Sodium (2.8 g, 0.12 mol) was added to ethanol (200 ml) to prepare sodium ethoxide, followed by adding diethyl (S)-2-methylbutylmalonate (40 g, 0.12 mol) and 4'-pentyl-4-biphenylylamidine hydrochloride (33.6 g, 0.11 mol), refluxing the mixture for 8 hours, adding acetic acid to make it acidic, filtering off deposited crystals, sufficiently washing with water and drying to obtain 5-(2'-methylbutyl)-2-(4'-pentyl-biphenyl-4-yl)-4,6-dihydroxypyrimidine (29.7 g).

Phosphorus oxychloride (94 g, 0.06 mol) was added to 5-(2'-methylbutyl)-2-(4'-pentyl-biphenyl-4-yl)-4,6-dihydroxypyrimidine (20 g, 0.06 mol) and N,N-diethylaniline (27.3 g, 0.18 mol), followed by refluxing the mixture for 20 hours, distilling off phosphorus oxychloride, introducing the residue into water, adding toluene, transferring the mixture into a separating funnel, sufficiently agitating it, sufficiently washing the resulting organic layer with 2N-NaOH and then with water, distilling off toluene and recrystallizing the residue from ethanol to obtain 5-(2'-methylbutyl)-2-(4'-pentyl-biphenyl-4-yl)-4,6-dichloropyrimidine (16.6 g), which was dissolved in ethanol and reduced in the presence of Pd/C to obtain the objective (S)-5-2'-methylbutyl)-2-(4'-pentyl-biphenyl-4-yl)pyrimidine (12.8 g). This product exhibited liquid crystalline properties and exhibited the following phase transition points (also see Table 1):

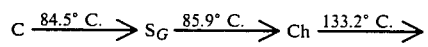

EXAMPLES 5 (USE EXAMPLE 1)

A liquid crystal composition consisting of the following liquid crystal compounds was prepared:

| Compound | % |
|---|---|
| $C_6H_{17}O-\bigcirc-\bigcirc_N^N-C_8H_{17}$ | 30% by weight |
| $C_8H_{17}O-\bigcirc-\bigcirc_N^N-C_8H_{17}$ | 20% by weight |
| $C_9H_{17}O-\bigcirc-\bigcirc_N^N-C_8H_{17}$ | 10% by weight |
| $C_{10}H_{21}O-\bigcirc-\bigcirc_N^N-C_8H_{17}$ | 10% by weight |
| $C_5H_{11}-\bigcirc-\bigcirc-\bigcirc_N^N-C_8H_{17}$ | 20% by weight |
| $C_7H_{15}-\bigcirc-\bigcirc-\bigcirc_N^N-C_8H_{17}$ | 10% by weight |

The phase transition points of the above liquid crystal composition are as follows:

Compound No. 47 as a compound of the present invention was added in 20% by weight to 80% by weight of the above liquid crystal composition to prepare a chiral smectic liquid crystal composition. Its phase transition points were as follows:

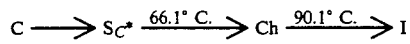

Further, the spontaneous polarization value and tilt angle of the liquid crystal composition were 40.8 nC/cm$^2$ and 25.4° at 25° C., respectively.

This liquid crystal composition was filled in a cell of 2 μm thick provided with transparent electrodes each obtained by coating the surface with PVA (polyvinyl alcohol) as an aligning agent and rubbing the resulting surface to subject it to a parallel aligning treatment, and the resulting liquid crystal element was placed between a polarizer and an analyzer crossed to each other and a voltage of 8 V was impressed. As a result, change in the intensity of transmitted light was confirmed.

The response time was sought from the change in the intensity of transmitted light at that time. The time was as follows:

| Temperature (°C.) | 61.1 | 56.1 | 50.0 | 45.0 | 40.0 | 35.0 | 30.0 | 25.0 |
|---|---|---|---|---|---|---|---|---|
| Response time (μsec) | 28 | 37 | 48 | 56 | 68 | 76 | 100 | 125 |

From the foregoing, it is seen that the compound of the present invention is a very useful ferroelectric liquid crystal material.

EXAMPLE 6 (USE EXAMPLE 2)

A liquid crystal composition consisting of the following liquid crystal compounds was prepared:

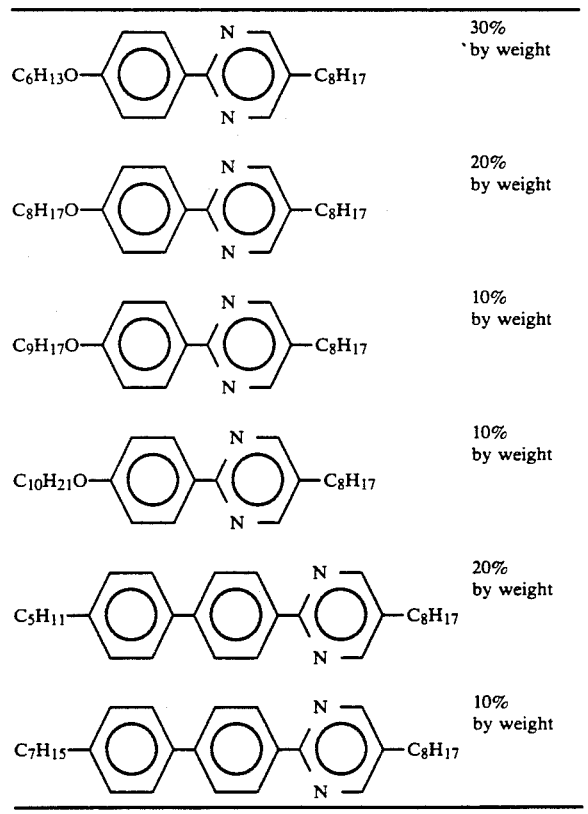

The phase transition points of the above composition are as follows:

A compound (No. 27) of the present invention was added in 20% by weight to 80% by weight of the above composition to prepare a chiral smectic liquid crystal composition. Its phase transition points were as follows:

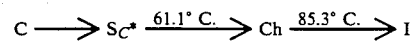

The spontaneous polarization value and tilt angle of this composition were 20.1 nC/cm$^2$ and 26.5° at 25° C., respectively. This composition was filled in a cell of 2 μm thick provided with transparent electrodes each obtained by coating the surface with PVA (polyvinyl alcohol) as an aligning agent and rubbing the resulting surface to subject it to a parallel aligning treatment, followed by placing the resulting liquid crystal element between a polarizer and an analyzer crossed to each other and impressing a voltage of 8 V. As a result, change in the intensity of transmitted light was confirmed. The response time sought from the change in the intensity of transmitted light at that time was as follows:

| Temperature (°C.) | 56.1 | 51.1 | 50 | 45 | 40 | 35 | 30 | 25 |
|---|---|---|---|---|---|---|---|---|
| Response time (μsec) | 52 | 69 | 71 | 88 | 104 | 125 | 151 | 200 |

From the foregoing, it is seen that the compound of the present invention is a very useful ferroelectric liquid crystal material.

EXAMPLE 7 (USE EXAMPLE 3)

A nematic liquid crystal composition consisting of

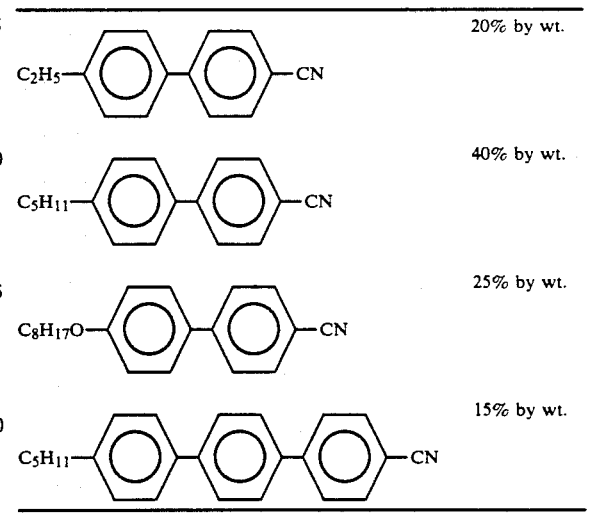

was filled in a cell having a distance between electrodes of 10 μm to prepare a TN mode display cell, which was obserbed under a polarizing microscope. As a result, a reverse twist domain was observed to be formed. In addition, as to the used cell, polyvinyl alcohol as an aligning agent was coated and the resulting surface was rubbed to subject it to an aligning treatment.

To the above nematic liquid crystal composition was added a compound (No. 5) of the present invention in 0.1% by weight, and with a similar TN cell, observation was carried out. As a result, the reverse twist domain was dissolved and a uniform nematic phase was observed.

EXAMPLE 8 (USE EXAMPLE 1)

To a nematic liquid crystal composition (commercially available ZLI 1132 made by Merck Company was used) was added a compound (No. 26) of the present invention in 1% by weight to prepare a chiral nematic liquid crystal composition, which was then filled in a cell having a distance between electrodes of 10 μm to observe the resulting cell under a polarizing microscope. As a result, the helical pitch was observed as follows:

| Temperature (°C.) | 20 | 30 | 40 | 50 | 60 | 70 |
|---|---|---|---|---|---|---|
| Pitch length (μm) | 11.6 | 11.7 | 11.8 | 12.1 | 12.3 | 12.3 |

As seen from the above results, the temperature-dependency of the pitch was very flat and the compound of the present invention is a superior agent for adjusting the pitch of chiral nematic liquid crystal compositions.

What we claim is:

1. An optically active compound expressed by the formula

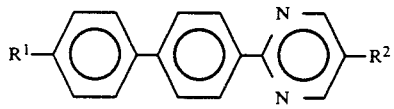
(1)

wherein one of $R^1$ and $R^2$ represents a straight chain alkyl or alkoxy group of 1 to 20 carbon atoms and the other represents an optically active 2-alkoxypropoxy, 2-alkanoyloxypropoxy, 2-alkoxypropionyloxypropoxy, 2-fluoroalkoxy, alkanoyloxy or alkoxypropionyloxy group.

2. A chiral nematic liquid crystal composition comprising at least two components at least one of which is an optically active compound according to claim 1.

3. An optically active compound according to claim 1, wherein the optically active group is an optically active 2-alkoxypropoxy group.

4. An optically active compound according to claim 1 wherein said optically active group is of the structure $$-OCH_2-CH(CH_3)-OC(O)R^3$$

in which $R^3$ is a straight chain alkyl group of 3 to 10 carbon atoms.

5. An optically active compound according to claim 4 wherein $R^2$ is an optically active group as defined.

6. An optically active compound according to claim 1, wherein said optically active group is of the structure $$-OCH_2-CH(CH_3)-OC(O)R^4$$

in which $R^4$ is an optically active alkyl group with one methyl branching.

7. An optically active compound according to claim 6, wherein $R^2$ is an optically active group as defined in claim 6.

8. An optically active compound according to claim 1, wherein said optically active group is of the structure $$-OCH_2-CH(CH_3)-OC(O)-CH(CH_3)-OR^5$$

in which $R^5$ is an alkyl group of 3 to 10 carbon atoms.

9. An optically active compound according to claim 8, wherein $R^2$ is an optically active group as defined in claim 8.

10. An optically active compound according to claim 1, wherein said optically active group is of the structure $$-OC(O)-CH(CH_3)-OR^7$$

in which $R^7$ is an alkyl group of 4 to 7 carbon atoms.

11. An optically active compound according to claim 1, wherein said optically active group is of the structure $$-OCH_2-CH(F)-R^6$$

in which $R^6$ is a straight chain alkyl of 5 to 7 carbon atoms.

12. A chiral nematic liquid crystal composition comprising at least two components at least one of which is an optically active compound, in which said optically active compound is a compound as defined in claim 4.

* * * * *